United States Patent [19]

Shillington

[11] Patent Number: 5,024,327

[45] Date of Patent: Jun. 18, 1991

[54] RESTRICTED ACCESS OPENING FOR DISPOSABLE SHARPS CONTAINERS

[75] Inventor: Richard A. Shillington, Leucadia, Calif.

[73] Assignee: Med-Safe Systems, Inc., Carlsbad, Calif.

[21] Appl. No.: 499,021

[22] Filed: Mar. 26, 1990

[51] Int. Cl.⁵ .............................................. B65D 85/24
[52] U.S. Cl. .................................. 206/366; 220/229; 220/910
[58] Field of Search ....................... 206/365, 366, 370; 220/229, 908, 909, 910

[56] References Cited

U.S. PATENT DOCUMENTS

| | | | |
|---|---|---|---|
| 3,342,319 | 9/1967 | Faulsei | 206/365 |
| 4,452,358 | 6/1984 | Simpson | 206/366 |
| 4,494,652 | 1/1985 | Nelson et al. | 206/366 |
| 4,502,606 | 3/1985 | Shillington et al. | 220/229 X |
| 4,520,926 | 6/1985 | Nelson | 206/366 |
| 4,600,112 | 7/1986 | Shillington et al. | 206/366 X |
| 4,702,385 | 10/1987 | Shillington et al. | 220/408 X |
| 4,816,307 | 3/1989 | Honeycutt | 206/366 X |
| 4,842,138 | 6/1989 | Sandel et al. | 206/366 X |
| 4,844,245 | 7/1989 | Bennett | 206/366 |

Primary Examiner—Jimmy G. Foster
Assistant Examiner—Jacob K. Ackun
Attorney, Agent, or Firm—Baker, Maxham, Jester & Meador

[57] ABSTRACT

A limited access closure cover for an opening in a top of a disposable sharps container comprises a frame for securing to the periphery of an open top of a container, an opening in the cover, the opening having the configuration of a cross section axial view of the syringe body, and finger flanges on the syringe body for receiving the axial passage of the body of a hypodermic syringe when angularly oriented to conform thereto.

17 Claims, 2 Drawing Sheets

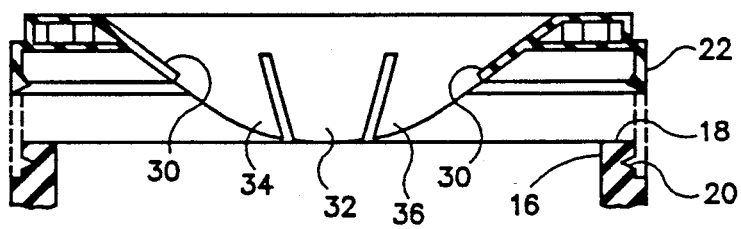
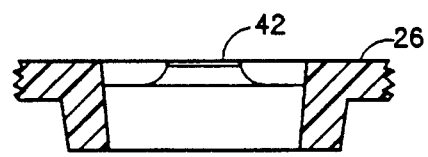
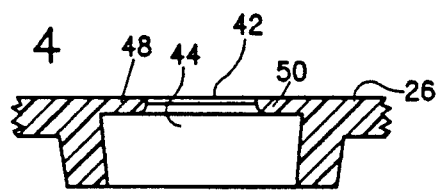
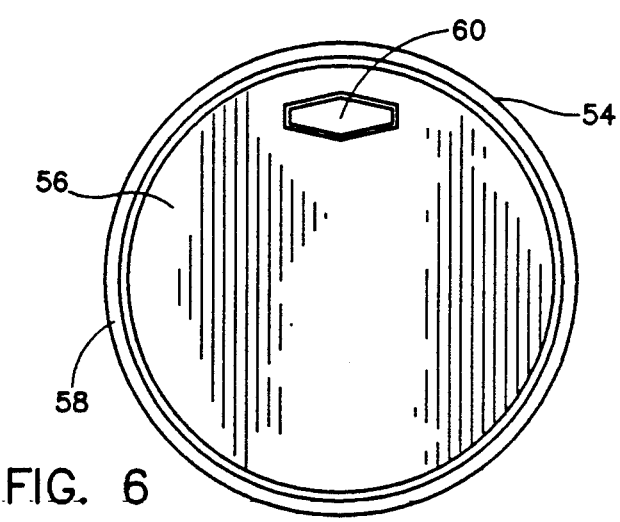

RESTRICTED ACCESS OPENING FOR DISPOSABLE SHARPS CONTAINERS

BACKGROUND OF THE INVENTION

The present invention relates to disposable sharps containers and pertains particularly to an improved restricted access opening for disposable sharps containers.

Disposable containers have been developed in recent years which provide a reasonably high degree of security for disposable articles and materials from hospitals and clinics. Many of these articles, such as needles and surgical blades known as sharps, and other similar articles and materials, must be disposed of in a manner to keep them out of the hands of unauthorized persons and to keep them from being reused. These containers are designed with access openings and closures to prevent the removal of materials from the container under ordinary circumstances.

One such container of the aforementioned type is that of our prior U.S. Pat. No. 4,502,606, issued Mar. 5, 1985, and directed to a locking closure for disposable containers. These containers are also provided with needle removal tools in the form of one or more slots which act as a wrench for removal of the needles from syringes and the like. These needle removal tools are not only convenient, but also provide a safe means for removal of the needle. The safe removal of the needle is essential to protect hospital personnel from certain highly contagious diseases.

Many prior disposable containers have had needle removal tools built into the top thereof adjacent the disposal opening. This is a convenient and desirable arrangement. However, The prior tools, while normally suitable for most needles, are not normally adequate for all existing needles. Due to the variations in sizes of the needle hubs, many needles do not fit the prior art devices with suitable accuracy. This results in wear of the removal slot due to the loose fit, frequently resulting in failure of the removal slot prior to filling of the container.

It is, therefore, desirable that a disposable container be available which has a limited access opening, and includes a reliable needle removal device as well as reliable closure security.

SUMMARY AND OBJECTS OF THE INVENTION

It is the primary object of the present invention to provide an improved sharps container having an improved restricted access opening.

In accordance with a primary aspect of the present invention, a cover having an annular rim for securing to the periphery of an open top of a container includes an opening having the configuration of a cross section axial view of a hypodermic syringe body and finger flanges on the syringe body for receiving the axial passage of the hypodermic syringe body when angularly oriented to conform thereto.

BRIEF DESCRIPTION OF THE DRAWING

The above and other objects and advantages of the present invention will become apparent from the following description when read in conjunction with the accompanying drawings wherein:

FIG. 3 is a front elevation view taken on line 3—3 of FIG. 1;

FIG. 4 is a section view taken on line 4—4 of FIG. 2;

FIG. 5 is a section view taken on line 5—5 of FIG. 2; and

FIG. 6 is a view like FIG. 2 of an alternate embodiment.

DETAILED DESCRIPTION OF A PREFERRED EMBODIMENT

Figure 1:
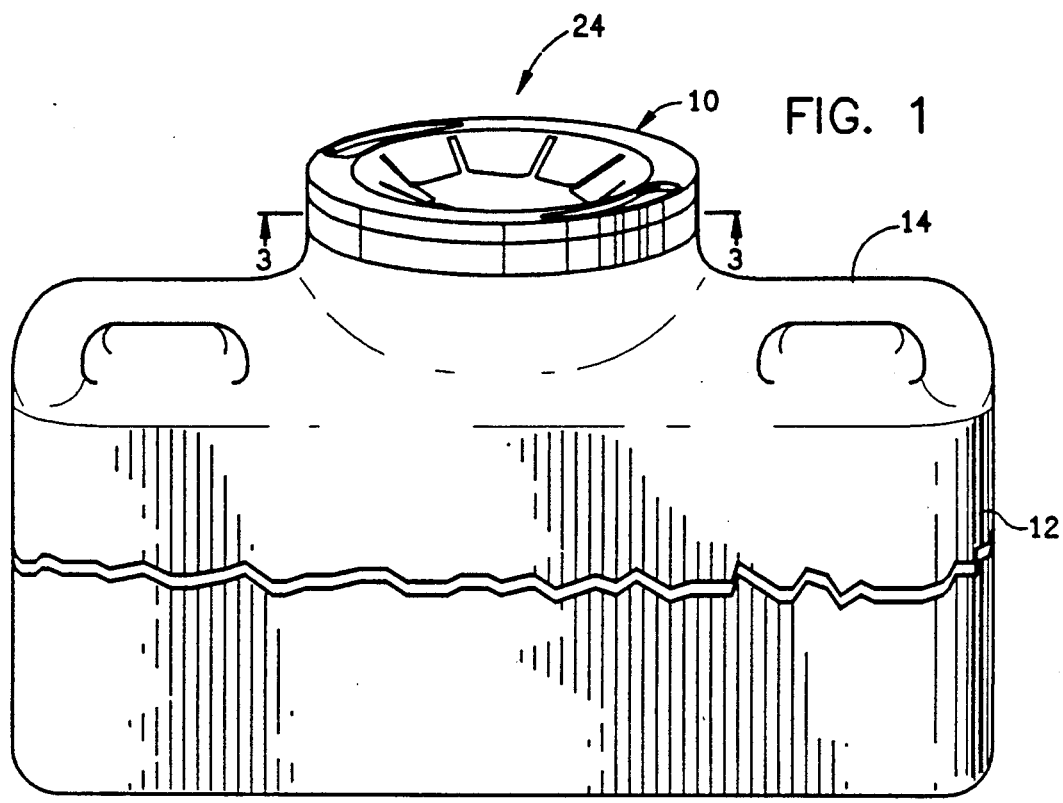
FIG. 1 is a perspective view illustrating a preferred embodiment of the invention.
Figure 2:
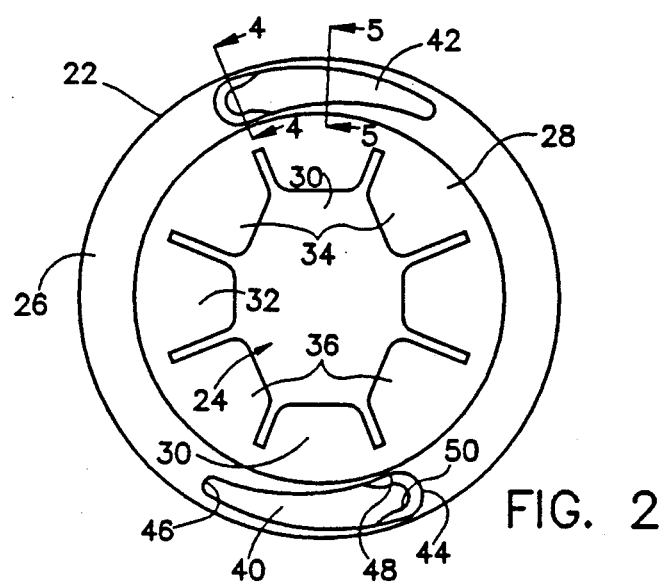
FIG. 2 is a top plan view of the embodiment of FIG. 1.

Referring to FIGS. 1-3, a preferred embodiment of the invention is illustrated. In the illustrated embodiment, a cap 24, in accordance with the invention, is mounted on a top opening of a disposable container 12. The overall container assembly, designated generally by the numeral 10, comprises a disposable container 12 having the usual bottom and upstanding sidewalls terminating at the top in a peripheral rim surrounding an upwardly directed opening. The illustrated embodiment may also have handles 14, as illustrated, formed of loops which may also serve to secure the container to mounting means or the like.

Referring to FIG. 3, the container has an upper generally circular opening defined by a peripheral rim 18. This peripheral rim has a locking groove 20, as described and covered in my prior U.S. Pat. No. 4,502,606 dated Mar. 5, 1985, and No. 4,600,112 dated July 15, 1986, for receiving a downwardly depending rim 22 of a cap assembly 24 having a cooperative locking lip or rim.

Referring again to FIG. 1, the container 12 has a top cap forming a restricted opening assembly, designated generally by the numeral 24. The top cap assembly 24 has an outer generally circular configuration conforming to that of the top opening of the container 12. The restricted opening assembly, designated generally by the numeral 24, comprises in the preferred embodiment a combination restricted access opening and closure assembly, as generally described above. Referring to FIG. 2, the restricted opening assembly comprises a generally circular planar rim section 26 having a downwardly depending connecting flange 22, as described above and shown in FIG. 3. The opening assembly 24 has the general configuration of that of a syringe body having a pair of outwardly directed finger flanges when a syringe is viewed along its axis. This is the conventional syringe construction, and the present invention takes advantage of that construction to provide an opening for receiving disposed of syringes, and limiting access thereof for the retrieval of spent and/or contaminated syringes.

The configuration of the opening requires that a syringe with finger flanges larger than the opening will have to be carefully oriented to conform to the configuration of the opening in order to pass into the container through the opening. Similarly, any effort to remove a syringe will require it to be similarly oriented. If the syringe is larger than the opening, the construction of the flaps forming the opening, as will be explained, resists the removal of the syringe and at the same time discourages the insertion of a hand for retrieval of a syringe.

The opening is formed by the inner edges of a plurality of flaps of different sizes and configurations, formed integrally with an inner inverted frustoconical panel section 28 of the cover. The inner panel 28 is slotted to form a pair of identical opposing flaps 30, a pair of opposing identical opposed flaps 32 and pairs 34 and 36, respectively, of opposed asymmetrical flaps. The inner edges of these flaps, which are semi-rigid as in my prior patent, form the central opening through which the disposable syringes must pass. The opening, however, is of a size to accept any number of sharps articles or products and to resist the insertion of a hand or the like for retrieval of the articles.

A typical opening, for example, will have a large diameter or dimension between the inner edges of flaps 30 of about 1.55 inches. The narrow dimension being that between the inner tips of flaps 32 will be on the order of about 1.16 inches.

As shown in FIG. 3, the flaps slope downward toward the interior of the container. This provides in essence a one-way closure permitting articles to pass in one direction into the container, yet resists the passage of articles in the opposite direction. It will be appreciated that articles greater in size than the actual opening can pass through the opening by biasing the flaps to the side and passing into the container. However, in the opposite direction, the flaps cannot ordinarily be deflected to accommodate the passage or removal of an article. As the flaps are biased axially outward, the tips move inward toward the axis of the opening restricting it.

The opening can be sized for particular size syringes so that only specific size syringes are disposed of in any specific containers. This approach is practical in situations where only a specific size of syringe is used in a particular location. It is also possible that different size containers with different size openings would be available for the different size syringes. This would reduce the possibility that smaller syringes could be placed in a container with a larger opening and retrieved.

In many instances, it is desirable to move the needle from the syringe and dispose of the needle separately, or so that the syringe may be reused. In other instances, it may be desirable simply to remove the needle when the syringe is being disposed of. The container top, in accordance with the invention, is provided with needle removal slots 40 and 42 disposed on opposite sides of the top and extending in opposite directions. These needle removal slots have a generally a tear-drop configuration and curved around the curvature of the top as illustrated. These slots act as wrenches with converging side walls for engaging the hub of the needle, so that the barrel of the syringe can be rotated for applying torque for removing the needle. The slot 40, for example, has a larger diameter at a larger end 44, with a smaller diameter at the opposite end 46. The larger diameter end of the opening may have a diameter on the order of about 0.36 inches, with the smaller end having a diameter of about 0.13 inches in diameter. The sides of the slot converge downward from the maximum diameter end to the minimum diameter end, providing opposed converging wrench surfaces for engaging opposite sides of the needle hub for engaging and removing the same.

A needle removal or pulling device in the form of a pair of fingernail like edges 48 and 50 extend inward from opposite sides of the slot at the large end 44, as illustrated in FIG. 2. When the needle is unthreaded, but fails to fall out of the opening of the barrel of the syringe, the syringe is pulled to the large end of the slot, such that the thin edges 48 and 50 extend between the end of the needle hub and the barrel of the syringe, such that lifting of the barrel dislodges the needle from the threaded bore thereof.

Referring to FIG. 6, an alternate top or cover with a syringe disposal opening is illustrated for a syringe disposal container for syringes of a specific size. In the illustrated embodiment, a cover 54 for fitting on an upwardly opened rim of an opening of a container is illustrated. This cover is a generally circular disc configuration having a center panel portion 56 and outer rim 58 for attachment to the container, as in the prior embodiment. A restricted syringe receiving opening 60 is disposed or formed in and through the inner panel portion 56 of the cover. This syringe opening has the configuration of a syringe with finger flanges when viewed along the syringe axis. The opening is sized to be just slightly larger than that of the syringe finger flanges so that the syringe can pass into the container when properly oriented. This container opening is designed for specific size of syringes only, such as for example, the smaller type commonly used by drug addicts. These syringes are on the order of about 50 cc in size and are widely used and available. This construction provides a simple inexpensive means for disposal of these widely available inexpensive syringes. The configuration of the opening enables selective insertion of the syringes with proper angular orientation, but provides such restricted and limited access that retrieval of a syringe is very difficult.

The opening may be located in any desired location around the surface area of the top. The typical syringe has a finger flange at the top of the barrel, such that when the plunger is forced to its innermost position for ejecting fluid from the barrel, the finger flange presents at the outer end the largest radial size of the barrel. Therefore, removal of syringes is difficult and requires a precise location of the syringe and angular orientation of the barrel of the syringe.

While I have illustrated and described my invention by means of specific embodiments, it is to be understood that numerous changes and modifications may be made therein without departing from the spirit and scope of the invention as defined in the appended claims.

I claim:

1. A limited access closure cover for an opening in a top of a disposable sharps container, comprising:
   an annular rim for securing to the periphery of an open top of a container;
   an opening in said closure, said opening having the configuration of a cross section axial view of a hypodermic syringe body and finger flanges on the syringe body for receiving the axial passage of the hypodermic syringe body when angularly oriented to conform thereto, said opening including an oblong central area and a plurality of radial slots extending outwardly therefrom.

2. A limited access closure cover for an opening in a top of a disposable sharps container according to claim 1 wherein:
   said opening being sized for receiving syringes of a predetermined size and slightly larger than the outer periphery of the finger flange of said syringes.

3. A limited access closure cover for an opening in a top of a disposable sharps container according to claim 2 wherein:
   said opening sized to receive only syringe bodies of 50 cc size.

4. A limited access closure cover for an opening in a top of a disposable sharps container according to claim 1 wherein:

said opening being sized for receiving syringes of a predetermined size and having inwardly directed flaps whereby the opening is smaller than the cross sectional area of a finger flange and syringe body of said predetermined size to enable passage thereof.

5. A limited access closure cover for an opening in a top of a disposable sharps container according to claim 4 wherein:

top has tear-drop shaped needle removal slot having a large end and a small end and opposed side walls tapering down to the small end.

6. A limited access closure cover for an opening in a top of a disposable sharps container according to claim 5 wherein:

said slot having inwardly directed opposed needle hub engaging fingernail-like edges at the large end.

7. A limited access closure cover for an opening in a top of a disposable sharps container according to claim 1 wherein:

said opening is sized for receiving syringes of a predetermined size and defined by inwardly and downwardly directed flaps so that the opening is smaller than the cross sectional area of a finger flange and syringe body of said predetermined size to enable one-way passage thereof into a container.

8. A limited access closure cover for an opening in a top of a disposable sharps container according to claim 7 wherein:

said top has a pair of tear-drop shaped needle removal slots on opposite sides of said opening, said slots having a large end and a small end and opposed side walls converge substantially uniformly down to the small end.

9. A limited access closure cover for an opening in a top of a disposable sharps container according to claim 8 wherein:

said slot having inwardly directed opposed needle hub engaging fingernail-like edges at the large end.

10. The combination of a disposable container having a limited access closure cover for an opening therein, comprising;

a disposable container having a top and an opening at the top; and a cover for said top having a syringe body receiving opening for receiving a syringe body having outwardly directed finger flanges, said opening having the configuration of an axial view of a syringe body having finger flanges for enabling the axial passage of the hypodermic syringe body when angularly oriented to conform thereto, said opening including an oblong central area and a plurality of radial slots extending outwardly therefrom.

11. The combination of a disposable container according to claim 10 wherein:

said opening is sized for receiving syringes of a predetermined size and slightly larger than the outer periphery of the syringe body and the finger flange of said predetermined size.

12. The combination of a disposable container according to claim 11 wherein:

said opening sized to receive only syringe bodies of 50 cc size.

13. The combination of a disposable container according to claim 10 wherein:

said opening si sized for receiving syringes of a predetermined size and having inwardly directed flaps so that the opening is smaller than the cross sectional area of a finger flange and syringe body of said predetermined size to enable passage thereof.

14. The combination of a disposable container according to claim 13 wherein:

said top has tear-drop shaped needle removal slot having a large end and a small end and opposed side walls tapering down to the small end.

15. The combination of a disposable container according to claim 14 wherein:

said slot having inwardly directed opposed needle hub engaging fingernail like edges at the large end.

16. A limited access closure cover for an opening in a top of a disposable sharps container, comprising:

a cover having an annular rim for securing to the periphery of a circular open top of a container;

an opening in said cover, said opening having the configuration of a cross section axial view of a hypodermic syringe body and finger flanges on the syringe body for receiving the axial passage of the hypodermic syringe body when angularly oriented to conform thereto; and said opening is sized for receiving syringes of a predetermined size and defined by inwardly and downwardly directed flaps so that the opening is smaller than the cross sectional area of a finger flange and syringe body of said predetermined size to enable one-way passage thereof into a container, said opening including an oblong central area and a plurality of radial slots extending outwardly therefrom.

17. A limited access closure cover for an opening in a top of a disposable sharps container according to claim 16 wherein:

said top has a pair of tear-drop shaped needle removal slots on opposite sides of said opening, said slots having a large end and a small end and opposed side walls converge substantially uniformly down to the small end; and inwardly directed opposed needle hub engaging fingernail like edges at the large end for engaging between the end of a needle hub and the end of a barrel for pulling the needle from the barrel.

* * * * *